United States Patent
Garnavi et al.

(10) Patent No.: US 10,169,872 B2
(45) Date of Patent: Jan. 1, 2019

(54) CLASSIFICATION OF SEVERITY OF PATHOLOGICAL CONDITION USING HYBRID IMAGE REPRESENTATION

(71) Applicant: International Business Machines Corporation, Armonk, NY (US)

(72) Inventors: Rahil Garnavi, Macleod (AU); Dwarikanath Mahapatra, Melbourne (AU); Pallab Roy, Kingsville (AU); Suman Sedai, Melbourne (AU); Ruwan B. Tennakoon, Hawthorn (AU)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/426,634

(22) Filed: Feb. 7, 2017

(65) Prior Publication Data

US 2018/0122068 A1    May 3, 2018

Related U.S. Application Data

(60) Provisional application No. 62/416,473, filed on Nov. 2, 2016.

(51) Int. Cl.
G06K 9/00 (2006.01)
G06T 7/00 (2017.01)
(Continued)

(52) U.S. Cl.
CPC ............ *G06T 7/0012* (2013.01); *A61B 3/12* (2013.01); *G06K 9/4676* (2013.01); *G06K 9/6269* (2013.01); *G06T 2207/30041* (2013.01)

(58) Field of Classification Search
None
See application file for complete search history.

(56) References Cited

U.S. PATENT DOCUMENTS 8,515,201 B1 * 8/2013 Murray Herrera .... G06K 9/527
                                                              382/100
9,008,391 B1    4/2015 Solanki et al.
(Continued)

FOREIGN PATENT DOCUMENTS

GB       2467840 A       8/2010
WO      03020112 A2      3/2003

OTHER PUBLICATIONS

C.P. Wilkinson et al., "Proposed International Clinical Diabetic Retinopathy and Diabetic Macular Edema Disease Severity Scales," Opthalmology, Sep. 2003, pp. 1677-1682, vol. 110, No. 9.
(Continued)

*Primary Examiner* — Idowu O Osifade
(74) *Attorney, Agent, or Firm* — David M. Quinn; Ryan, Mason & Lewis, LLP

(57) ABSTRACT

A computer-implemented method obtains at least one image from which severity of a given pathological condition presented in the at least one image is to be classified. The method generates a hybrid image representation of the at least one obtained image. The hybrid image representation comprises a concatenation of a discriminative pathology histogram, a generative pathology histogram, and a fully connected representation of a trained baseline convolutional neural network. The hybrid image representation is used to train a classifier to classify the severity of the given pathological condition presented in the at least one image. One non-limiting example of a pathological condition whose severity can be classified with the above method is diabetic retinopathy.

20 Claims, 8 Drawing Sheets

(51) Int. Cl.
G06K 9/62 (2006.01)
G06K 9/46 (2006.01)
A61B 3/12 (2006.01)

(56) References Cited

U.S. PATENT DOCUMENTS

2002/0052551 A1    5/2002  Sinclair et al.
2015/0065803 A1*   3/2015  Douglas ............ A61B 1/00009
                                                          600/200

OTHER PUBLICATIONS

E. Chaum et al., "Automated Diagnosis of Retinopathy by Content-Based Image Retrieval," Retina, Nov./Dec. 2008, pp. 1463-1477, vol. 28, No. 10.
A.D. Fleming et al., "The Role of Haemorrhage and Exudate Detection in Automated Grading of Diabetic Retinopathy," British Journal of Opthalmology, Jun. 2010, pp. 706-711, vol. 94, No. 6.
M.D. Abramoff et al., "Automated Early Detection of Diabetic Retinopathy," Opthalmology, Jun. 2010, pp. 1147-1154, vol. 117, No. 6.
R. Pires et al., "Advancing Bag-of-Visual-Words Representations for Lesion Classification in Retinal Images," PLoS One, Jun. 2014, 12 pages, vol. 9, No. 6.
M.D. Abramoff et al., "Improved Automated Detection of Diabetic Retinopathy on a Publicly Available Dataset Through Integration of Deep Learning," Investigative Opthalmology & Visual Science, Oct. 2016, pp. 5200-5206, vol. 57, No. 13.
E.S. Varnousfaderani et al., "Diabetic Retinopathy Detection from Image to Classification Using Deep Convolutional Neural Network," Investigative Opthalmology & Visual Science, Sep. 2016, p. 5961, vol. 57, No. 12.
A. Krizhevsky et al., "ImageNet Classification with Deep Convolutional Neural Networks," Proceedings of the 25th International Conference on Neural Information Processing Systems (NIPS), Dec. 2012, pp. 1097-1105.
"Diabetic Retinopathy Detection, Identify Signs of Diabetic Retinopathy in Eye Images," https://www.kaggle.com/c/diabetic-retinopathy-detection, Feb.-Jul. 2015, 2 pages.
J. De Fauw, "Detecting Diabetic Retinopathy in Eye Images," http://blog/kaggle.com/2015/08/10/detecting-diabetic-retinopathy-in-eye-images/, Aug. 10, 2015, 40 pages.
A. Liaw et al., "Classification and Regression by randomForest," R News, Dec. 2002, pp. 18-22, vol. 2, No. 3.
K. Simonyan et al., "Very Deep Convolutional Networks for Large-Scale Image Recognition," arXiv:1409.1556v6, Sep. 2015, 14 pages.
O. Russakovsky et al., "ImageNet Large Scale Visual Recognition Challenge," International Journal of Computer Vision, Dec. 2015, pp. 211-252, vol. 115, No. 3.
G. Csurka et al., "Visual Categorization with Bags of Keypoints," Workshop on Statistical Learning in Computer Vision (ECCV), May 2004, pp. 1-2, vol. 1, No. 1-22.
Tom Verhoeff, "Delay-Insensitive Codes—An Overview," Distributed Computing, Mar. 1988, pp. 1-8, vol. 3, No. 1.
J.A.K. Syukens et al., "Least Squares Support Vector Machine Classifiers," Neural Processing Letters, Jun. 1999, pp. 293-300, vol. 9, No. 3.
J. Sanchez et al., "Image Classification with the Fisher Vector: Theory and Practice," International Journal of Computer Vision, Dec. 2013, pp. 222-245, vol. 105, No. 3.
F. Perronnin et al., "Improving the Fisher Kernel for Large-Scale Image Classification," Proceedings of the 11th European Conference on Computer Vision (ECCV), Part IV, Sep. 2010, pp. 143-156.
"Diabetic Retinopathy Detection, Evaluation," https://www.kaggle.com/c/diabetic-retinopathy-detection/details/evaluation, Feb.-Jul. 2015, 2 pages.
E. Oh et al., "Diabetic Retinopathy Risk Prediction for Fundus Examination Using Sparse Learning: a Cross Sectional Study," BMC Medical Informatics and Decision Making, Jan. 2013, 14 pages, vol. 13, No. 1.
Wikipedia, "Bag-of-Words Model in Computer Vision," https://en.wikipedia.org/w/index.php?title=Bag-of-words_model_in_computer_vision&printable=yes, Sep. 10, 2016, 5 pages.

* cited by examiner

| 21.5cm DR SEVERITY | PRECISION | | RECALL | | SCORE | |
|---|---|---|---|---|---|---|
| | CNN | PHM | CNN | PHM | CNN | PHM |
| 0 | 0.92 | 0.92 | 0.97 | 0.98 | 0.94 | 0.95 |
| 1 | 0.40 | 0.59 | 0.28 | 0.21 | 0.33 | 0.29 |
| 2 | 0.06 | 0.62 | 0.34 | 0.26 | 0.11 | 0.31 |
| 3 | 0.50 | 0.72 | 0.11 | 0.83 | 0.18 | 0.77 |
| 4 | 0.69 | 0.92 | 0.59 | 0.61 | 0.63 | 0.72 |

| METHOD | QUADRATIC WEIGHTED KAPPA SCORE |
|---|---|
| PHM | 0.86 |
| CNN | 0.81 |

CLASSIFICATION OF SEVERITY OF PATHOLOGICAL CONDITION USING HYBRID IMAGE REPRESENTATION

CROSS-REFERENCE TO RELATED APPLICATION(S)

The present application claims the benefit of and priority to U.S. Provisional Application Ser. No. 62/416,473, filed on Nov. 2, 2016 and entitled "Classification of Severity of Pathological Condition Using Hybrid Image Representation," the entirety of which is incorporated by reference herein for all purposes.

BACKGROUND

The pathological condition known as diabetic retinopathy (DR) affects the blood circulation system in the eye. DR is the most common cause of vision loss among people with diabetes and the leading cause of vision impairment and blindness among working-age people. DR typically progresses through four stages: mild non-proliferative DR; moderate non-proliferative DR; severe non-proliferative DR; and proliferative DR.

Early detection of DR is crucial to prevent vision loss. However, access to an ophthalmology specialist is limited in rural or isolated geographic regions thus reducing the chance of early diagnosis of DR.

SUMMARY

Embodiments provide techniques for classification of severity of a pathological condition using a hybrid image representation.

In one embodiment, a method comprises the following steps. The method obtains at least one image from which severity of a given pathological condition presented in the at least one image is to be classified. The method generates a hybrid image representation of the at least one obtained image. The hybrid image representation comprises a concatenation of a discriminative pathology histogram, a generative pathology histogram, and a fully connected representation of a trained baseline convolutional neural network. The hybrid image representation is used to train a classifier to classify the severity of the given pathological condition presented in the at least one image. The obtaining and generating steps are performed by a computing device comprising a processor coupled to a memory.

In another embodiment, an apparatus comprises at least one processor and a memory operatively coupled to the processor and configured to: obtain at least one image from which severity of a given pathological condition presented in the at least one image is to be classified; and generate a hybrid image representation of the at least one obtained image, wherein the hybrid image representation comprises a concatenation of a discriminative pathology histogram, a generative pathology histogram, and a fully connected representation of a trained baseline convolutional neural network, and wherein the hybrid image representation is used to train a classifier to classify the severity of the given pathological condition presented in the at least one image.

In yet another embodiment, a computer program product comprises a processor-readable storage medium having encoded therein executable code of one or more software programs, wherein the one or more software programs when executed by the one or more processors implement steps of: obtaining at least one image from which severity of a given pathological condition presented in the at least one image is to be classified; and generating a hybrid image representation of the at least one obtained image, wherein the hybrid image representation comprises a concatenation of a discriminative pathology histogram, a generative pathology histogram, and a fully connected representation of a trained baseline convolutional neural network, and wherein the hybrid image representation is used to train a classifier to classify the severity of the given pathological condition presented in the at least one image.

Advantageously, illustrative embodiments provide improved techniques for computer-aided diagnosis of a pathological condition such as DR by automatically classifying the severity of DR using a hybrid image representation.

These and other exemplary embodiments of the invention will be described in or become apparent from the following detailed description of exemplary embodiments, which is to be read in connection with the accompanying drawings.

BRIEF DESCRIPTION OF THE DRAWINGS

FIG. 5 depicts experimental results of a convolutional neural network-based base line method and a proposed hybrid method for severity classification of diabetic retinopathy according to an embodiment of the invention.

DETAILED DESCRIPTION

Illustrative embodiments will be described below for severity classification of diabetic retinopathy (DR). However, it is to be understood that embodiments of the invention may be applied to pathological conditions other than DR.

Before describing illustrative embodiments of the invention, some existing DR severity classification approaches will be discussed.

As mentioned above, DR affects the blood circulation system in the eye, and is the most common cause of vision loss among people with diabetes and the leading cause of vision impairment and blindness among working-age people. DR typically progresses through four stages of the fundus portion of the eye (i.e., part of the eyeball opposite the pupil).

Figure 1:
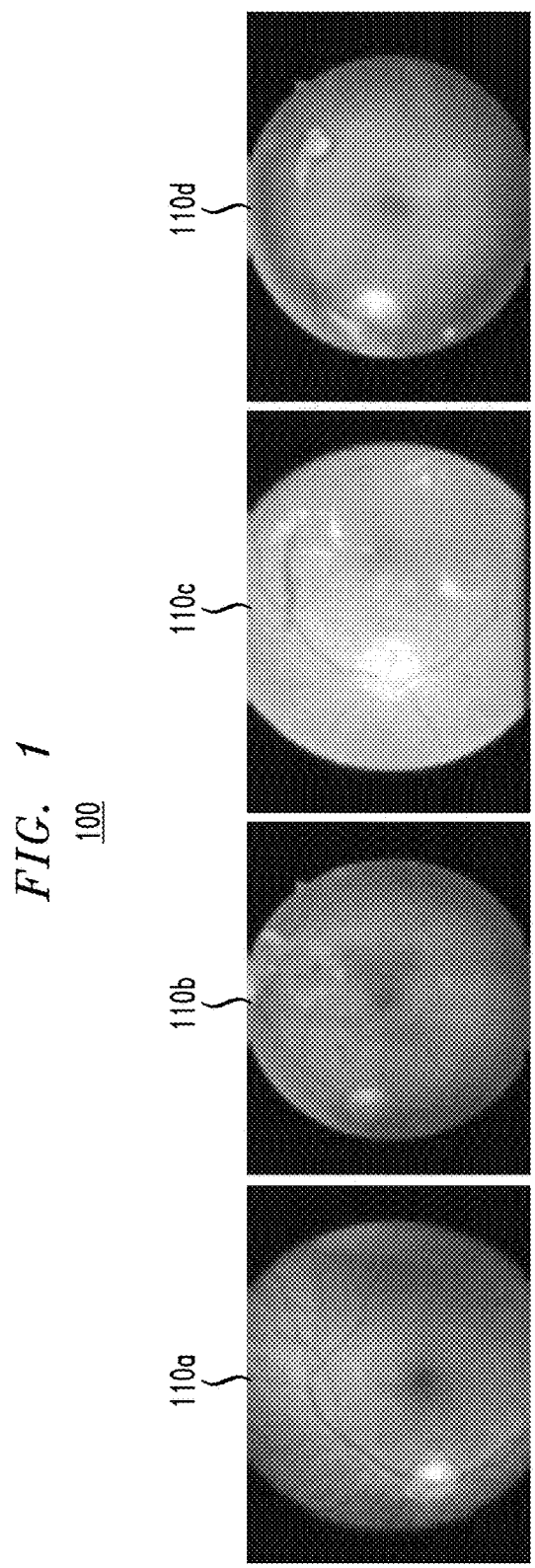
FIG. 1 depicts images of the fundus portion of an eye illustrating diabetic retinopathy progress through four stages.

With reference to FIG. 1, a retinal image set 100 is shown illustrating four stages of DR progress. The images of the retinal image set 100 include: mild non-proliferative DR 110(a); moderate non-proliferative DR 110(b); severe non-proliferative DR 110(c); and proliferative DR 110(d).

Early detection of DR is crucial to prevent vision loss. However, access to an ophthalmology specialist is limited in rural or isolated geographic regions, thus reducing the chance of early diagnosis of DR. Computer-aided diagnosis may solve that dilemma by automatically classifying the severity of DR.

A number of computer-aided methods have been proposed for DR severity classification. These methods can be divided into two group such as: (a) a classical image analysis-based method; and (b) a deep learning-based method. A deep learning-based method, such as a convolutional neural network (CNN) method, has been highly successful in a large number of computer vision and image analysis tasks, substantially outperforming all classical image analysis techniques. Indeed, the highest performing algorithms in the recent Kaggle DR severity classification competition, which completed July 2015, all used CNNs to identify signs of DR in retinal images.

CNN-based DR classification methods can be divided into two groups: image-based CNN; and pathology-based CNN. Image-based CNN learns features from the whole image through forward and backward processes in a deep layer structure for DR severity prediction. In contrast to that, pathology-based CNN learns a separate CNN network for each DR related pathology such as hemorrhage, exudates, etc. Finally, for an input image, the filter responses of each pathology-specific CNN network are combined to predict the DR severity.

Both of these existing DR severity prediction methods have some limitations. Image-based CNN methods downsample the input retinal image because of graphical processing unit (GPU) memory constraints. As a consequence, the information of the subtle DR pathologies, such as a microaneurysm, might be lost. On the contrary, pathology specific CNN methods require a large number of manually annotated pathology patches which are expensive and time consuming.

As used herein, the term patch refers to a region of an image. For example, a patch may be a rectangular region. The patch may be cropped, for example, from the center of the pathology location given by the expert retinal image grader. An image may be comprised of a given number of non-overlapping patches. Accordingly, an image may be reconstructed from non-overlapping patches associated with the image.

To overcome the limitations of the two existing approaches, as well as other limitations, embodiments of the invention provide a hybrid method where an image-based CNN feature is combined with pathology driven generative and discriminative bag-of-words (BoW) image representations, which require less number of manually annotated pathology patches. As is known, the BoW model can be applied to image classification by treating image features as words. In document classification, a bag of words is a sparse vector of occurrence counts of words, i.e., a sparse histogram over the vocabulary. In computer vision, a bag of (visual) words is a vector of occurrence counts of a vocabulary of local image features. Computer vision is an interdisciplinary field that relates to the use of computers to gain high-level understanding from digital images or videos, i.e., computer vision technology attempts to automatically perform tasks that the human visual system can perform.

Embodiments of the invention provide many advantages including, but not limited to: (1) discriminative BoW representation of the retinal image based on DR related pathology; (2) generative BoW representation of the retinal image based on DR related pathology; and (3) an efficient feature vector containing CNN-based fully-connected representation and pathology specific discriminative and generative representation of the retinal image for DR severity classification.

Figure 2:
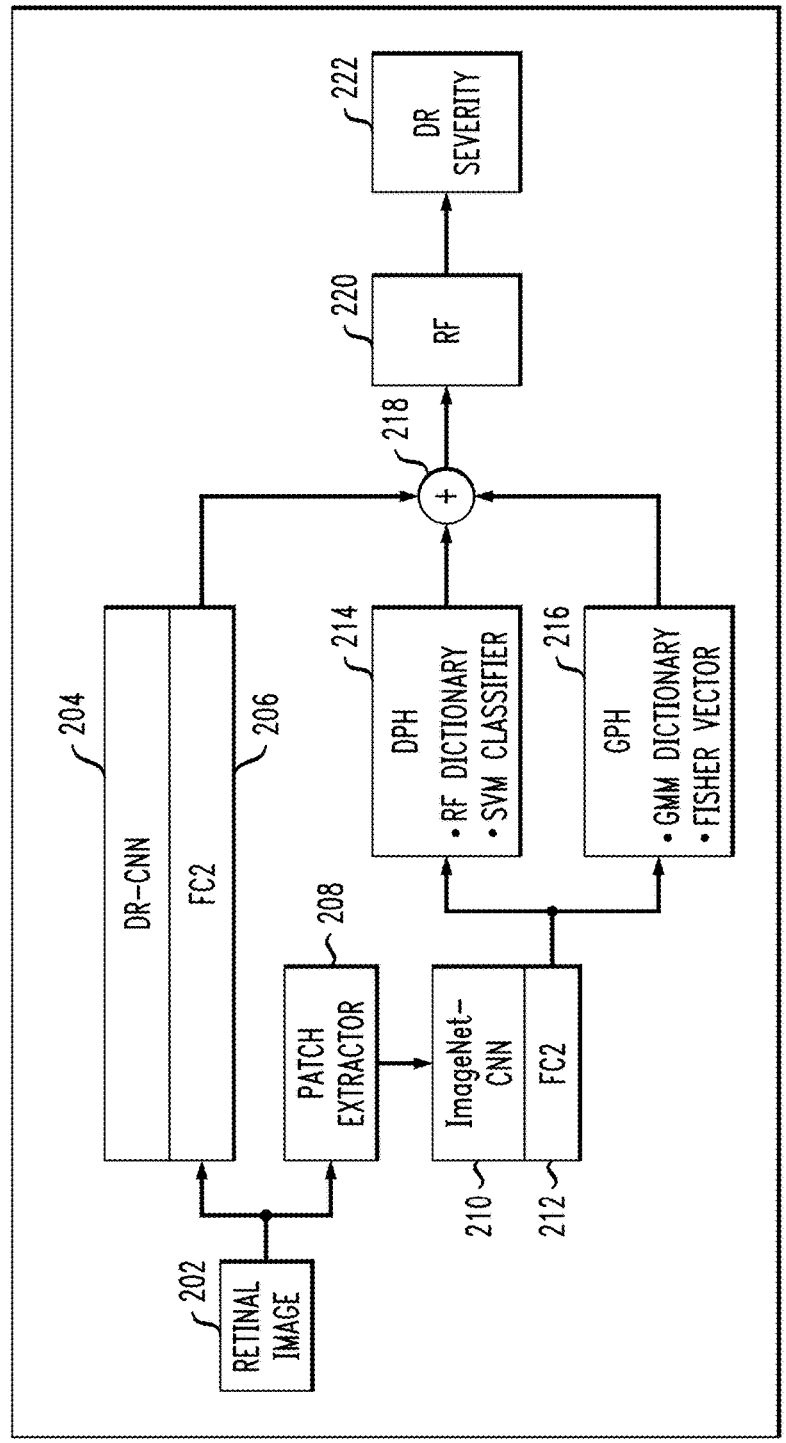
FIG. 2 depicts a flow diagram of a methodology for severity classification of diabetic retinopathy according to an embodiment of the invention.

A DR severity classification method according to an illustrative embodiment is depicted in system flow diagram 200 in FIG. 2. It is to be appreciated that a retinal image such as one of the images shown in FIG. 1 serve as input to the classification methodology. In the methodology, as shown in FIG. 2, a pre-trained DR-CNN model 204 (trained for DR severity classification) is used to compute a fully connected layer response (DR-FC2 response 206) from input retinal image 202. The input retinal image 202 may comprise retinal images taken of both a left eye and a right eye, or may comprise a retinal image taken of a single eye. In parallel to that, a patch extractor 208 is used to obtain non-overlapping patches from the input retinal image 202.

The obtained non-overlapping patches are then propagated through a pre-trained ImageNet-CNN model 210 (trained for object classification) to obtain one or more fully connected layer responses (FC2 response(s) 212). Following that, the FC2 response(s) 212 are passed through proposed discriminative pathology histogram (DPH) and generative pathology histogram (GPH) modules 214 and 216, respectively, to compute the pathology driven image level representations such as a DPH response and a GPH response respectively. In one embodiment, and as shown in FIG. 2, DPH module 214 may utilize a random forest (RF) dictionary and a (linear) support vector machine (SVM) classifier, and GPH module 216 may utilize a Gaussian Mixture Model (GMM) dictionary and at least one Fisher vector. Finally, the concatenated hybrid representation of the DR-FC2, DPH, GPH responses, concatenated hybrid representation 218, is fed into an RF classifier 220 for DR severity classification, which outputs a DR severity 222. Further details regarding the RF dictionary, RF classifier, SVM classifier, GMM dictionary and Fisher vector will be discussed below with reference to FIG. 3.

Figure 3:
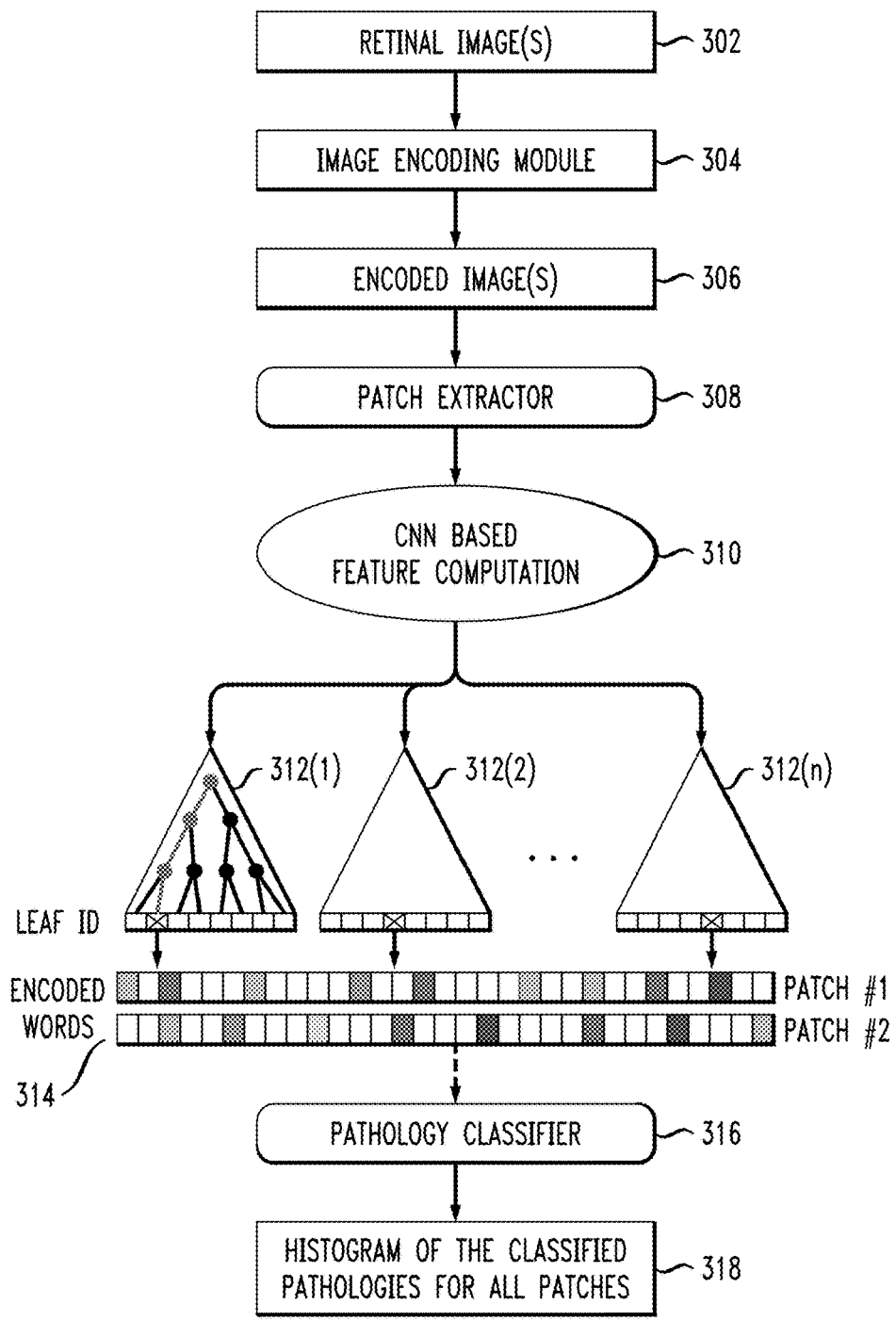
FIG. 3 depicts an algorithm for computation of a discriminative pathology histogram for severity classification of diabetic retinopathy according to an embodiment of the invention.

With reference to FIG. 3, a system flow diagram 300 of the discriminative pathology histogram (DPH) computation procedure according to an illustrative embodiment is presented. A local patch-based image encoding module, 304, takes retinal image(s) 302 as input. Then, a patch extractor 308 extracts and obtains a set of non-overlapping local regions of size n×n (patches) from encoded image(s) 306 output by image encoding module 304. The details of the feature extraction, encoding and classification of the patches into healthy and different pathology classes and computation of the distribution (histogram) of the healthy and different pathology patches for a given retinal image is described in the following sub-sections.

Computation of patch feature descriptor. The extracted non-overlapping patches are passed through a CNN-based feature computation module 310, which may utilize a pre-trained CNN model (e.g., VGG Net trained on an imagenet dataset is used in an illustrative experiment). Then, a fully connected representation (FCR) of the extracted non-overlapping input patches is obtained by forward-propagating them through the CNN network, which gives a feature vector of length 4096 for each patch.

Encoding of patch descriptors using RF dictionary. The method obtains a bag of words (BoW) representation of the feature descriptors for each patch. A random forest (RF) classifier is used as a dictionary for encoding the feature descriptors. The random forest is an ensemble of decision trees, shown in FIG. 3 as comprising n trees 312(1)-312(n), trained by random sampling of the training data and features. During the training stage, each node in a tree is assigned a binary test that is applicable to any data sample. Based on the result of the test, a sample can go to one of the two children of a given non-leaf node and finally end up in a leaf node. In a random forest, samples end up in the same leaf node, if the subsets of their feature dimensions are close. Hence, if two data samples are close (similar feature vectors), then they should fall into close leaf nodes in a random forest. In illustrative embodiments, random forest is used for clustering the feature descriptors of each patch. As shown in FIG. 3, the feature descriptor of each patch is pushed through each decision tree 312(1)-312(n) of the random forest. Since the forest has n number of trees thus for each patch, we will get a vector of length n, where each element of the vector represents the identifier (ID) of the leaf node for the corresponding tree Then, the method applies one-hot-encoding on the obtained vector, one-hot-encoding is necessary for the proper representation of the distinct elements of the vector. In one embodiment, the number of trees is set to n=1000. The expert graded pathology and healthy patches are used to obtain a random forest dictionary 314.

Computation of pathology histogram. After the encoding step, as explained immediately above, the extracted non-overlapping local patches of an image are represented by:

$$X=\{x_j\}, j\in\{1, 2, \ldots, N\}$$

where $x_j \in R^d$ is an encoded local patch. The method computes the probability of the presence of a pathology in a patch by a function $f.R^d \rightarrow R^M, f(x_j)\alpha_j$, that takes the individual local descriptors $x_j$ and maps them onto a pathology class $\alpha_j$. The assignment of each patch to a pathology class can be done by the following function:

$$á_{m,j}=1, if f(x_j)=m, \text{ where } m\in\{pa_0, pa_1, pa_2, pa_3, pa_4\}$$

Here, $pa_0$, $pa_1$, $pa_2$, $pa_3$, and $pa_4$ represent healthy, micro-aneurysm, hemorrhage, exudate, and neovascularization affected patches, respectively, Finally, a histogram of the pathologies 318 is computed by using the following equation:

$$H(m) = \frac{\sum_j \alpha_{m,j}}{|j|} \quad (1)$$

Here, $f(.)$ is a pathology classifier 316. In one embodiment, the pathology classifier is a linear support vector machine (SVM)-based classifier trained on expert annotated pathology patches (healthy, micro-aneurysm, hemorrhage, exudate and neovascularization) of five different types. Fully connected representations of 20,000 patches sampled from the expert graded training patches of different pathologies and healthy regions are equally divided into two groups to train the RF dictionary 314 and the pathology classifier 316.

For a generative pathology histogram, the method obtains a generative BoW image level representation per input image using at least one Fisher vector based on the non-overlapping patches. A Fisher vector models the distribution of the patch descriptors using a Gaussian Mixture Model (GMM) and represents an image by considering the gradient with respect to the GMM parameters. As is known in the art, a GMM is a parametric probability density function represented as a weighted sum of component Gaussian densities. The GMM parameters may be estimated from training data using one or more known estimation techniques.

As explained immediately above, the descriptor of the non-overlapping local patches of an image is represented by $$X=\{x_j\}, j\in\{1, 2, \ldots, N\}$$

where $x_j \in R^d$. The method first applies principal component analysis (PCA) to reduce the dimension of the fully connected representations and obtain x'. Let the pre-trained GMM with K Gaussians be represented by $U=\{u_k, k=1, \ldots K\}$ where $\lambda=\{\omega_k, \mu_k, \sigma_k, k=1, \ldots K\}$. In statistics, the score function is given by the gradient of the log-likelihood of the data on the model:

$$G_\lambda^x = \nabla_\lambda \log u_\lambda(x) \quad (2)$$

This gradient describes the contribution of the individual parameters to the generative process. In other words, it describes how the parameters of the generative model $u_j$» should be modified to better fit the data X. For each visual word $u_k$, two gradient vectors $G_{\mu_k} \in \mathfrak{R}^d$ and $G_{\sigma_k} \in \mathfrak{R}^d$, are computed by aggregating the gradients of the patch descriptors extracted from an image with respect to the mean and the standard deviation of the $k^{th}$ Gaussian. Then, a final image representation, Fisher vector (GPH), is obtained by concatenating all of the gradient vectors. Following the Improved Fisher Kernel framework, the method finally applies power normalization and $l_2$-normalization to the Fisher vector.

The dimensionality of each representation vector is reduced to 128 by PCA where a projection is trained with 20,000 fully connected representations sampled from expert graded training patches of different pathologies and healthy regions. A visual vocabulary (GMM of 256 Gaussian distributions) is also trained with the same samples.

Figure 4:
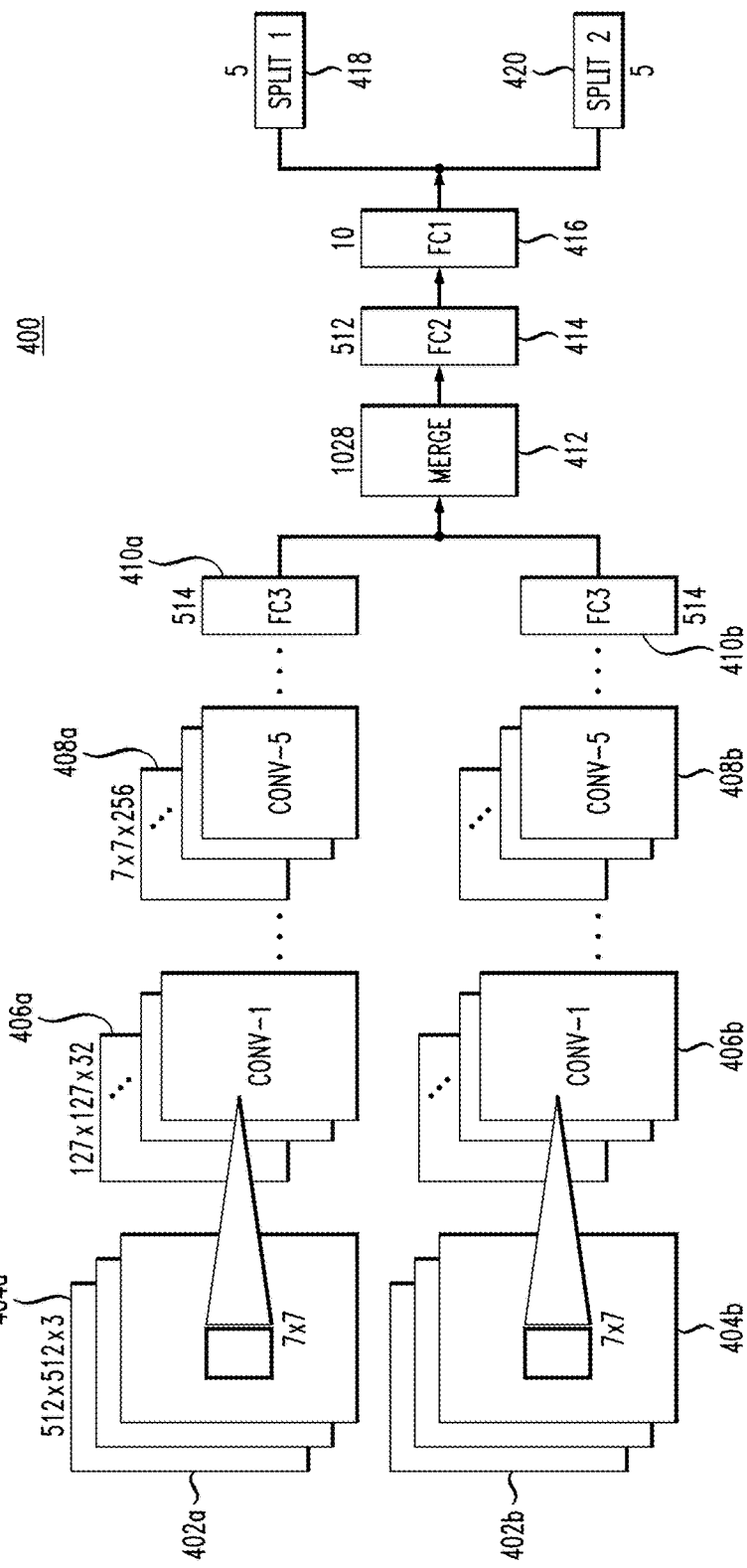
FIG. 4 depicts an architecture of a convolutional neural network used for obtaining a fully connected layer representation for severity classification of diabetic retinopathy according to an embodiment of the invention.

The fully connected layer representation from a CNN architecture (FCR2) is obtained, which was ranked as one of the top five methods in Diabetic Retinopathy Detection, Kaggle contest. FIG. 4 shows a high-level overview of a given CNN architecture 400. The given CNN architecture 400 will be described in the context of using retinal images from both the left eye and the right eye. However, in other embodiments, the CNN architecture may use retinal images from a single eye.

CNN architecture 400 is shown comprising CNN 402a and CNN 402b. In one embodiment, each CNN comprises an input layer, five convolution layers and a fully connected layer. As shown, CNN 402a comprises an input layer 404a, first convolution layer (Conv-1) 406a, fifth convolution layer (Conv-5) 408a, and a fully connected layer (FC3) 410a. CNN 402b is shown comprising an input layer 404b, Conv-1 406b, Conv-5 408b, and FC3 410b. As shown, each input layer 404a and 404b may have a receptive field of size 7×7, and each FC3 410a and 410b may have a size of 514. Although not explicitly shown, each convolution layer may have a receptive field of size 3×3.

The convolution stride ("stride"), which controls how depth columns around the spatial dimensions (e.g., width and height) are allocated, may be set to a value of 1. Spatial padding of the convolution layer input may be used to preserve the spatial resolution after each convolution operation. Following each convolution operation, spatial pooling may be carried out at the pool layer by performing max-pooling over a 2×2 receptive field, with stride 2.

As further depicted in FIG. 4, the FC3 activation of CNNs 402a and 402b may be concatenated by using a merge layer

412. The merge layer 412 may be followed by two fully connected layers of size 512 and 10, FC2 414 and FC1 416, respectively. Finally, reshape and softmax layers of size 5, shown as Split1 418 and Split2 420, may be used to train the model to predict the DR severity.

During the testing, the left and right eye images are propagated through the trained network to obtain the concatenated FC2 activation, and are then reshaped back into two eyes. For instance, as shown in FIG. 4 using both eyes, 512 responses are obtained from FC2 layer and reshaped into two representations containing 256 responses for the left eye and the right eye, respectively, for each patient.

As discussed with reference to FIG. 4, the input retinal images from the left and right eyes have been passed through two identical CNNs. Here, the output of both of these CNNs are combined to predict the DR severity. However, with some minor modification, each of these CNNs can be used to predict DR severity using only one eye (e.g., each FC3 may be followed by a fully connected and softmax layer).

The discriminative pathology histogram (DPH), generative pathology histogram (GPH) and fully connected representation (FCR2) are combined to create a hybrid feature representation of the image. Finally, a random forest (RF) classifier is trained using the hybrid feature representation to classify the severity of DR.

An evaluation dataset may contain 35126 high-resolution color retinal fundus images provided by EyePACS and made publicly available by Kaggle. The images may be taken under a variety of imaging conditions with different models of cameras, magnification, and image quality. Ninety percent of the images were randomly selected for training and the rest were used for testing.

With reference to FIG. 5, Table 500 represents the classification results of the proposed hybrid method (PHM) according to illustrative embodiments and baseline CNN-based DR severity prediction method (CNN). The Kaggle dataset has five classes of diabetic retinopathy (DR) such as: healthy (0); mild non-proliferative retinopathy (1); moderate non-proliferative retinopathy (2); severe non-proliferative retinopathy (3); and proliferative diabetic retinopathy (4). For each of these classes, the recall, precision and $F_1$ score are computed. Classification results show that PHM achieved better precision, recall and $F_1$ score for DR severity label 0, 1, 2, 3 and 4 compared to CNN. In the training dataset, classes are not evenly distributed and most of the training images belong to healthy class therefore both of these methods show high accuracy for the healthy class. Moreover, PHM is showing significantly higher classification accuracy for DR severity level 2, 3 and 4 compared to CNN. PHM is using pathology specific domain knowledge from high resolution image patches in addition to the CNN-based global feature, thus showing improvement in the granular classification of DR. The quadratic kappa score is also computed for both of these methods. Accordingly, PHM (kappa score =0.86) outperforms CNN (kappa score=0.81).

As described herein, illustrative embodiments provide a fusion of generative and discriminative bag-of-words image representation with fully connected representation of a convolutional neural network (CNN) for DR severity classification. The method incorporates pathological domain knowledge from a local perspective which is complementary to the state of the art CNN-based image features. The experimental results indicate that the proposed hybrid representation of the retinal image improve the DR classification accuracy on a granular level. Moreover, the proposed method, PHM, shows higher overall classification accuracy (quadratic kappa score of 0.86) compared to the baseline CNN-based method (0.81). In illustrative embodiments of the proposed hybrid method, the discriminative and generative pathology dictionaries are created by using the expert-graded pathology patches. As an alternative, the CNN network can be used for automatic sampling of the pathology and healthy patches.

Figure 6:
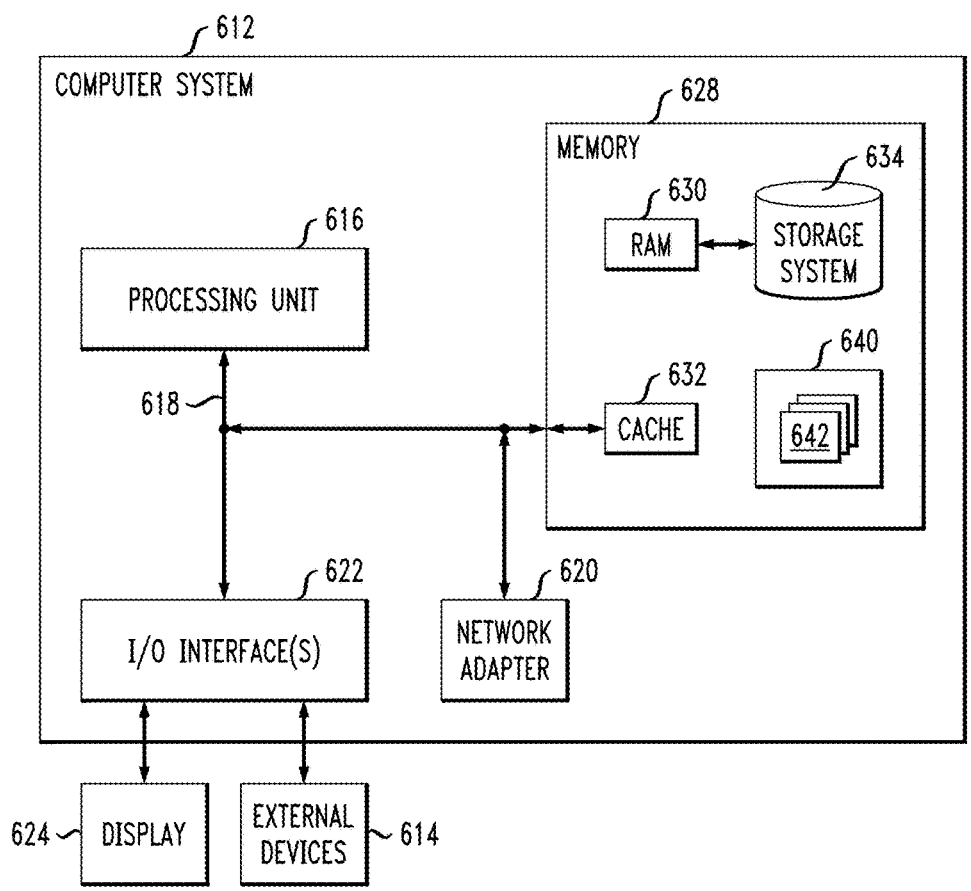
FIG. 6 depicts a computer system in accordance with which one or more components/steps of techniques of the invention may be implemented according to an embodiment of the invention.

One or more embodiments can make use of software running on a computer or workstation. With reference to FIG. 6, in a computing node 610 there is a system/server 612, which is operational with numerous other general purpose or special purpose computing system environments or configurations. Examples of well-known computing systems, environments, and/or configurations that may be suitable for use with system/server 612 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

System/server 612 may be described in the general context of computer system executable instructions, such as program modules, being executed by a computer system. Generally, program modules may include routines, programs, objects, components, logic, data structures, and so on that perform particular tasks or implement particular abstract data types. System/server 612 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, system/server 612 is shown in the form of a computing device. The components of system/server 612 may include, but are not limited to, one or more processors or processing units 616, system memory 628, and bus 618 that couples various system components including system memory 628 to processor 616.

Bus 618 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

System/server 612 typically includes a variety of computer system readable media. Such media may be any available media that is accessible by system/server 612, and it includes both volatile and non-volatile media, removable and non-removable media.

The system memory 628 can include computer system readable media in the form of volatile memory, such as random access memory (RAM) 630 and/or cache memory 632. System/server 612 may further include other removable/non-removable, volatile/nonvolatile computer system storage media. By way of example only, storage system 634 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 618 by one or more data media interfaces.

As depicted and described herein, memory 628 may include at least one program product having a set (e.g., at least one) of program modules that are configured to carry out the functions of embodiments of the invention. A program/utility 640, having a set (at least one) of program modules 642, may be stored in memory 628 by way of example, and not limitation, as well as an operating system, one or more application programs, other program modules, and program data. Each of the operating system, one or more application programs, other program modules, and program data or some combination thereof, may include an implementation of a networking environment. Program modules 642 generally carry out the functions and/or methodologies of embodiments of the invention as described herein.

System/server 612 may also communicate with one or more external devices 614 such as a keyboard, a pointing device, an external data storage device (e.g., a USB drive), display 624, one or more devices that enable a user to interact with system/server 612, and/or any devices (e.g., network card, modem, etc.) that enable system/server 612 to communicate with one or more other computing devices. Such communication can occur via I/O interfaces 622. Still yet, system/server 612 can communicate with one or more networks such as a LAN, a general WAN, and/or a public network (e.g., the Internet) via network adapter 620. As depicted, network adapter 620 communicates with the other components of system/server 612 via bus 618. It should be understood that although not shown, other hardware and/or software components could be used in conjunction with system/server 612. Examples include, but are not limited to, microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 7:
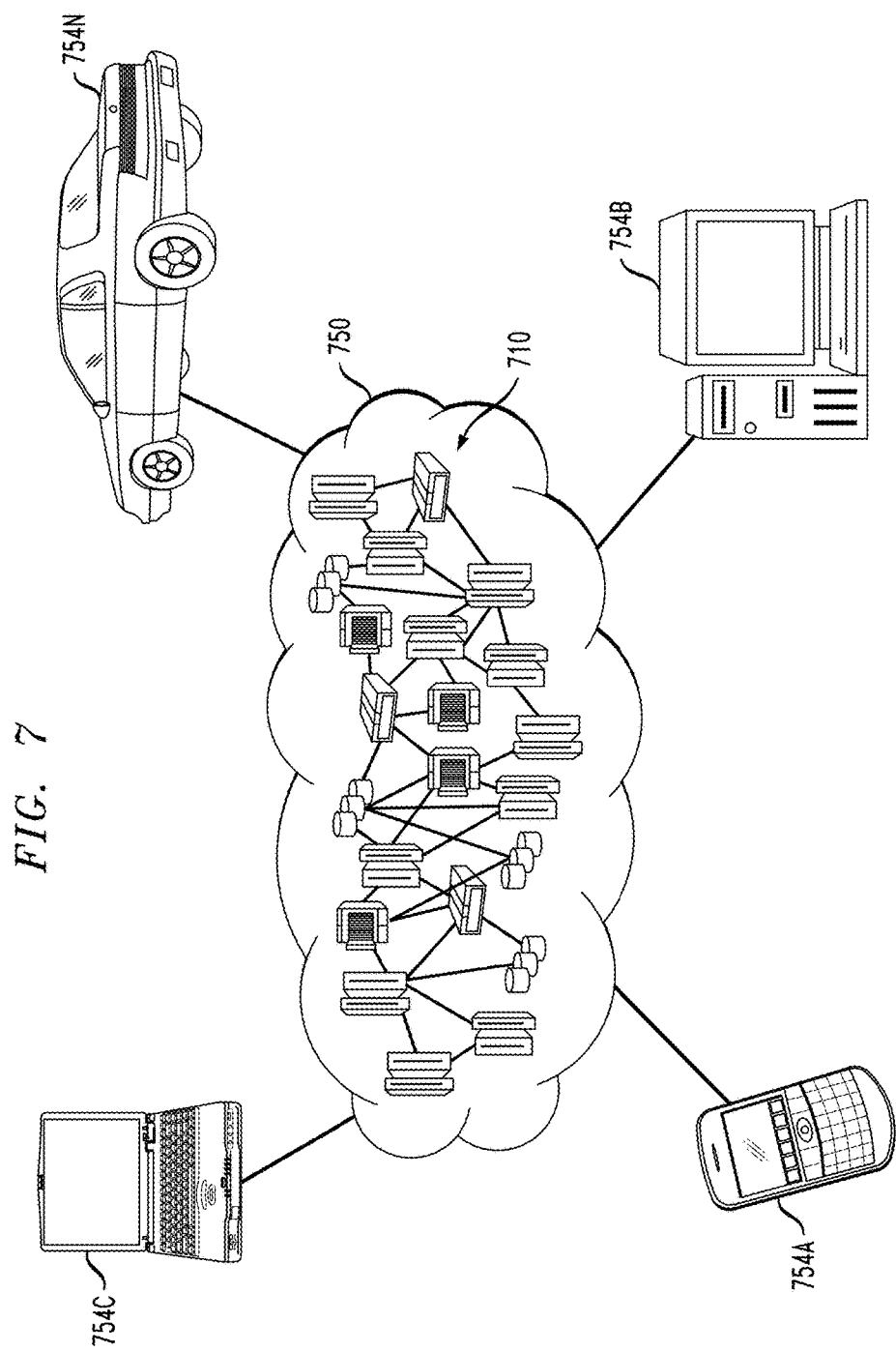
FIG. 7 depicts a cloud computing environment according to an embodiment of the invention.

Referring now to FIG. 7, an illustrative cloud computing environment 750 is depicted. As shown, cloud computing environment 750 includes one or more cloud computing nodes 710 with which local computing devices used by cloud consumers, such as, for example, personal digital assistant (PDA) or cellular telephone 754A, desktop computer 754B, laptop computer 754C, and/or automobile computer system 754N may communicate. Nodes 710 may communicate with one another. They may be grouped (not shown) physically or virtually, in one or more networks, such as Private, Community, Public, or Hybrid clouds as described hereinabove, or a combination thereof. This allows cloud computing environment 750 to offer infrastructure, platforms and/or software as services for which a cloud consumer does not need to maintain resources on a local computing device. It is understood that the types of computing devices 754A-N shown in FIG. 7 are intended to be illustrative only and that computing nodes 710 and cloud computing environment 750 can communicate with any type of computerized device over any type of network and/or network addressable connection (e.g., using a web browser).

Figure 8:
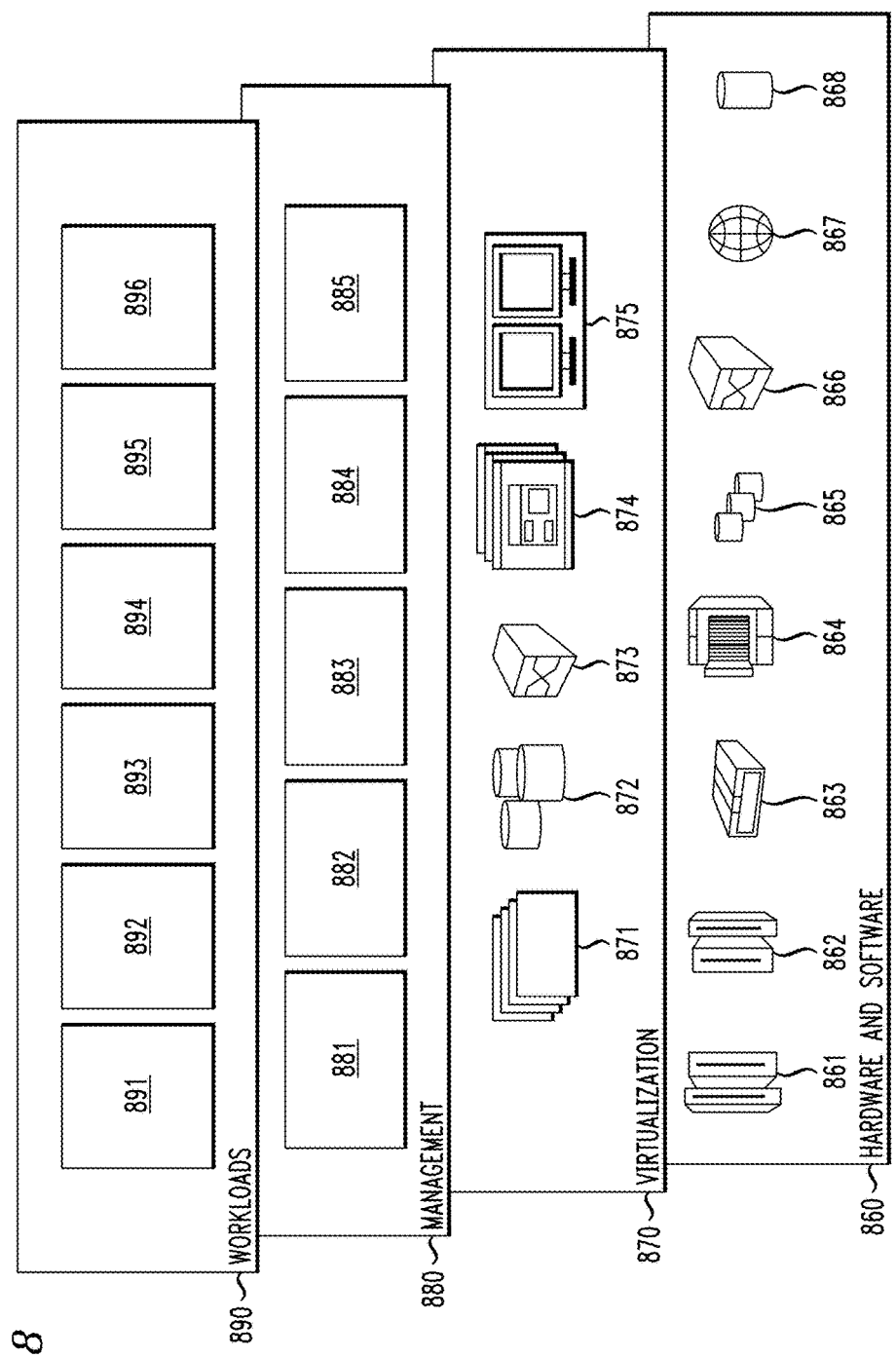
FIG. 8 depicts abstraction model layers according to an embodiment of the invention.

Referring now to FIG. 8, a set of functional abstraction layers provided by cloud computing environment 750 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 860 includes hardware and software components. Examples of hardware components include: mainframes 861; RISC (Reduced Instruction Set Computer) architecture based servers 862; servers 863; blade servers 864; storage devices 865; and networks and networking components 866. In some embodiments, software components include network application server software 867 and database software 868.

Virtualization layer 870 provides an abstraction layer from which the following examples of virtual entities may be provided: virtual servers 871; virtual storage 872; virtual networks 873, including virtual private networks; virtual applications and operating systems 874; and virtual clients 875.

In one example, management layer 880 may provide the functions described below. Resource provisioning 881 provides dynamic procurement of computing resources and other resources that are utilized to perform tasks within the cloud computing environment. Metering and Pricing 882 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 883 provides access to the cloud computing environment for consumers and system administrators. Service level management 884 provides cloud computing resource allocation and management such that required service levels are met. Service Level Agreement (SLA) planning and fulfillment 885 provide pre-arrangement for, and procurement of, cloud computing resources for which a future requirement is anticipated in accordance with an SLA.

Workloads layer 890 provides examples of functionality for which the cloud computing environment may be utilized. Examples of workloads and functions which may be provided from this layer include: transaction data capture 891; blockchain computation 892; data analytics processing 893; risk assessment 894; alert processing 895; and ameliorative/corrective/remedial action implementation 896, which may perform various functions described above.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Embodiments of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Note that given the distributed computing network illustrated in FIGS. 6-8, an image can be captured of a patient in an isolated geographic region and sent to one or more computing devices that implement the severity classification techniques using the hybrid image representation described herein in the context of FIGS. 1-5. Following classification of the severity of the pathological condition, e.g., a given non-proliferative or proliferative stage of DR, one or more messages can be sent back across the distributed network to the patient location to advise the patient (or a healthcare facility or professional) about the severity of the condition and the appropriate medical course of action for that condition. Of course, the entire image capture and severity classification procedure can occur on a single computing device or on multiple collocated computing devices. Embodiments of the invention are not limited to any particular computing platform.

Although illustrative embodiments have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method comprising:
obtaining, at a digital image processor, at least one image from which severity of a given pathological condition presented in the at least one image is to be classified; and
generating, at the digital image processor, a hybrid image representation of the at least one obtained image, wherein the hybrid image representation comprises a concatenation of a discriminative pathology histogram, a generative pathology histogram, and a fully connected representation of a trained baseline convolutional neural network, and further wherein the discriminative pathology histogram and the generative pathology histogram are each computed using a word occurrence count vector modeling process;
training a classifier using the hybrid image representation;
classifying the severity of the given pathological condition presented in the at least one image based on the trained classifier; and
wherein the steps of the method are performed by a computing device comprising a processor coupled to a memory.

2. The method of claim 1, wherein the given pathological condition presented in the at least one obtained image comprises diabetic retinopathy.

3. The method of claim 2, wherein the classifier classifies the diabetic retinopathy in the at least one obtained image into one of a plurality of diabetic retinopathy severity classifications.

4. The method of claim 1, wherein the classifier comprises a random forest classifier.

5. The method of claim 1 wherein the discriminative pathology histogram is computed utilizing a random forest dictionary and a linear support vector machine classifier and the generative pathology histogram is computed utilizing a Gaussian Mixture Model dictionary and at least one Fisher vector.

6. The method of claim 1, wherein generating the hybrid image representation further comprises extracting a set of patches from the at least one obtained image.

7. The method of claim 6, wherein generating the hybrid image representation further comprises passing the extracted set of patches through the trained baseline convolutional neural network to obtain a fully connected representation of the extracted set of patches in the form of a set of feature descriptors for each patch.

8. The method of claim 7, wherein generating the hybrid image representation further comprises encoding the set of feature descriptors for each patch using the classifier.

9. The method of claim 8, wherein the set of feature descriptors for each patch is encoded using the word occurrence count vector modeling process.

10. The method of claim 8, wherein generating the hybrid image representation further comprises clustering the encoded feature descriptors in each patch.

11. The method of claim 10, wherein generating the hybrid image representation further comprises computing the discriminative pathology histogram from the clustered feature descriptors.

12. An apparatus, comprising:
at least one processor; and
a memory operatively coupled to the processor and configured to:
obtain, at a digital image processor, at least one image from which severity of a given pathological condition presented in the at least one image is to be classified;
generate, at the digital image processor, a hybrid image representation of the at least one obtained image, wherein the hybrid image representation comprises a concatenation of a discriminative pathology histogram, a generative pathology histogram, and a fully connected representation of a trained baseline convolutional neural network, and further wherein the discriminative pathology histogram and the generative pathology histogram are each computed using a word occurrence count vector modeling process
train a classifier using the hybrid image representation; and
classify the severity of the given pathological condition presented in the at least one image based on the trained classifier.

13. A computer program product comprising a processor-readable storage medium having encoded therein executable code of one or more software programs, wherein the one or more software programs when executed by the one or more processors implement steps of:
obtaining, at a digital image processor, at least one image from which severity of a given pathological condition presented in the at least one image is to be classified;
generating, at the digital image processor, a hybrid image representation of the at least one obtained image, wherein the hybrid image representation comprises a concatenation of a discriminative pathology histogram, a generative pathology histogram, and a fully connected representation of a trained baseline convolutional neural network, and further wherein the discriminative pathology histogram and the generative pathology histogram are each computed using a word occurrence count vector modeling process;
training a classifier using the hybrid image representation; and
classifying the severity of the given pathological condition presented in the at least one image based on the trained classifier.

14. The computer program product of claim 13, wherein the given pathological condition presented in the at least one obtained image comprises diabetic retinopathy, and wherein the classifier classifies the diabetic retinopathy in the at least one obtained image into one of a plurality of diabetic retinopathy severity classifications.

15. The computer program product of claim 13, wherein the classifier comprises a random forest classifier.

16. The computer program product of claim 13, wherein the discriminative pathology histogram is computed utilizing a random forest dictionary and a linear support vector machine classifier and the generative pathology histogram is computed utilizing a Gaussian Mixture Model dictionary and at least one Fisher vector.

17. The computer program product of claim 13, wherein generating the hybrid image representation further comprises:
extracting a set of patches from the at least one obtained image;
passing the extracted set of patches through the trained baseline convolutional neural network to obtain a fully connected representation of the extracted set of patches in the form of a set of feature descriptors for each patch; and
encoding the set of feature descriptors for each patch using the classifier.

18. The computer program product of claim 17, wherein the set of feature descriptors for each patch is encoded using the word occurrence count vector modeling process.

19. The computer program product of claim 17, wherein generating the hybrid image representation further comprises clustering the encoded feature descriptors in each patch.

20. The computer program product of claim 19, wherein generating the hybrid image representation further comprises computing the discriminative pathology histogram from the clustered feature descriptors.

* * * * *